(12) United States Patent
Brodbeck et al.

(10) Patent No.: US 6,991,724 B2
(45) Date of Patent: Jan. 31, 2006

(54) WATER, SEDIMENT/FUEL SEPARATOR FOR FUEL CHECKER

(76) Inventors: Robert M. Brodbeck, 9310 S. Watson Gulch Rd., Littleton, CO (US) 80127; Charles A. Teilborg, 11452 SR 211, Usk, WA (US) 99180

( * ) Notice: Subject to any disclaimer, the term of this patent is extended or adjusted under 35 U.S.C. 154(b) by 251 days.

(21) Appl. No.: 10/723,868

(22) Filed: Nov. 26, 2003

(65) Prior Publication Data

US 2005/0109688 A1    May 26, 2005

(51) Int. Cl.
*B01D 35/02*    (2006.01)
*B01D 35/34*    (2006.01)

(52) U.S. Cl. ............... 210/232; 210/464; 210/466; 210/482; 73/61.72

(58) Field of Classification Search ........ 210/232, 210/464, 466, 482; 73/61.72
See application file for complete search history.

(56) References Cited

U.S. PATENT DOCUMENTS

| | | | | |
|---|---|---|---|---|
| 3,010,583 A | * | 11/1961 | Kenyon ............... 210/406 |
| 3,011,349 A | | 12/1961 | Kratz | |
| 3,063,289 A | * | 11/1962 | Moul ............... 73/61.72 |
| 3,503,250 A | * | 3/1970 | Cotton et al. ............... 73/61.72 |
| 3,976,572 A | * | 8/1976 | Reick ............... 210/94 |
| 4,956,298 A | * | 9/1990 | Diekmann ............... 435/293.1 |
| 5,359,905 A | | 11/1994 | Brodbeck | |

OTHER PUBLICATIONS

Wing Arrow Products, Inc.; The Gats Jar—Instruction Manual (3 Pages) 800.942.9464.

* cited by examiner

Primary Examiner—Thomas M. Lithgow
(74) Attorney, Agent, or Firm—Lawrence N. Ginsberg

(57) ABSTRACT

The filter assembly for a fuel checker includes a filter housing, a removable screen assembly, a first protective cap and a second protective cap. The filter housing includes a fuel receiving end portion and a fuel exiting end portion. The fuel receiving end portion is shaped to securely attach to a fuel checker. The filter housing defines a volume for containing checked fuel. A removable screen assembly is securely attachable to the fuel exiting end portion. The removable screen assembly includes a flexible screen housing and a filter screen supported by the flexible screen housing. The filter screen is a barrier to water and desired particulate debris. A first protective cap fits over the fuel receiving end portion for containing evaporative fumes while the filter assembly is being stored. A second protective cap fits over the removable screen assembly and protects the screen when the filter assembly is being stored.

14 Claims, 4 Drawing Sheets

WATER, SEDIMENT/FUEL SEPARATOR FOR FUEL CHECKER

BACKGROUND OF THE INVENTION

1. Field of the Invention

The present invention relates to fuel checkers for receiving specimens of fuel tank contents, and more particularly to a filter assembly designed for use in conjunction with fuel tank checkers.

2. Description of the Related Art

As a recognized safety precaution, the nature of the fuel in aircraft gas tanks must be checked before each flight to determine the presence of any contaminating agents as well as the octane rating. In the past, this inspection has been effected by, for example, the opening of the tank quick drain valve, by any suitable means in allowing a portion of the fuel to flow outwardly for reception within any convenient type of container. A scrutiny of the withdrawn fuel by an experienced individual will readily indicate whether the fuel is clear or is contaminated, and, further, as to what the octane rating of such fuel might be since its coloration is indicative thereof. In addition to withdrawing a specimen of the fuel from each tank of the aircraft, it is desired that a sample be taken from the lowermost location in the gas system, so that such procedure requires considerable time as well as effort in the requisite removal of any portions of the cowling to obtain access to the valve and operation of the valve itself.

Also, the like testing of fuels in the tank of gasoline powered ground vehicles, for example, in the military field, tanks, jeeps, half-tracks, and the like, is a desirable practice for assuming optimum operation. In the past this was accomplished by the use of any convenient instrumentalities, with all the associated inconvenience and time-consumption.

These tasks were made more convenient by the design of more specialized fuel checker devices. U.S. Pat. No. 3,011,349, issued to D. W. Kratz, entitled "Composite Tool and Receptacle", discloses a tool and receptacle for receiving specimens of aircraft gas tanks. The Kratz device utilizes an elongated body of circular cross-section with a closed lower end. The upper end edge is provided with a series of spaced apart, upwardly opening, generally U-shaped indentations or notches for engaging axially aligned actuating arms of a pet cock type quick drain valve. The elongated body is preferably formed of molded transparent plastic. The device has a screwdriver assembly integral to the bottom end of the elongated body which is handy during various operations typically involved with aircraft maintenance.

Present applicant, Robert M. Brodbeck, is the inventor of an improved fuel checker disclosed and claimed in U.S. Pat. No. 5,359,905, entitled Fuel Checker For Use With Pet Cock or Ball and Spring Drain Valves. The '905 apparatus comprises an elongated body of substantially circular cross-section. The body is fabricated of transparent molded material and is open at its upper end. The body is of tubular character through a portion of its length for defining a fuel-receiving compartment having a central axis and communicating with the open upper end of the body. The body has spaced-apart indentations in its upper end edge for alignment and cooperation with associated actuating arms of a pet cock drain valve, if such a pet cock drain valve is utilized. The tubular portion is closed at its lower end portion. A resilient semi-rigid rod is removably attached at a first end to the lower end portion of the tubular portion. The resilient rod extends along the central axis beyond the upper end edge of the body so as to engage and manipulate a ball and spring drain valve at a second end of the rod, if such a ball and spring drain valve is utilized. Additionally, the rod is supported at an intermediate portion thereof. Supporting the rod at the first end (lower end) provides much more effective use with ball and spring type drain valves making it much less flimsy and incapable of being pushed down the elongated body during use by the opposing force of the ball and spring valve.

Recently, the Environmental Protection Agency (EPA) has mandated that no fuel can be thrown out onto the tarmac ramp. Therefore, it has become desirable to pour the tested fuel back into the fuel tank. This is undesirable if the sample has water and/or other contaminants. Thus, one desires to filter out such contaminants and return the fuel to the tank.

In response to this problem Wing Aero Products, Inc. distributes what is referred to as "The GATS Jar". The GATS Jar is a stand alone fuel checker/separator device that provides both checking and separation of water and other contaminants. It includes a cap that supports a separator screen that creates a barrier to the passage of water through it and certain particulate debris, but remains no obstacle to the flow of fuel. The GATS Jar; however, has an open end so that while not in use it is difficult to store the device due to the resultant fumes and potential dripping of residual fuel from it. Furthermore, it includes a plastic plunger that makes it less than substantial.

SUMMARY OF THE INVENTION

In a broad aspect, the present invention is a filter assembly for a fuel checker including a filter housing, a removable screen assembly, a first protective cap and a second protective cap. The filter housing includes a fuel receiving end portion and a fuel exiting end portion. The fuel receiving end portion is shaped to securely attach to a fuel checker. The filter housing defines a volume for containing checked fuel. A removable screen assembly is securely attachable to the fuel exiting end portion. The removable screen assembly includes a flexible screen housing and a filter screen supported by the flexible screen housing. The filter screen is a barrier to water and desired particulate debris. A first protective cap fits over the fuel receiving end portion for containing evaporative fumes while the filter assembly is being stored. A second protective cap fits over the removable screen assembly and protects the screen when the filter assembly is being stored.

Use of the present invention has several advantages over the GATs Jar. It is compact and therefore can be easily stored. The filter housing is of one-piece construction and is very durable. It is entirely sealable when maintained in a stored mode. Therefore, fumes and residual fuel cannot leak. It is detachable from the fuel checker itself.

DETAILED DESCRIPTION OF THE INVENTION

Figure 1:
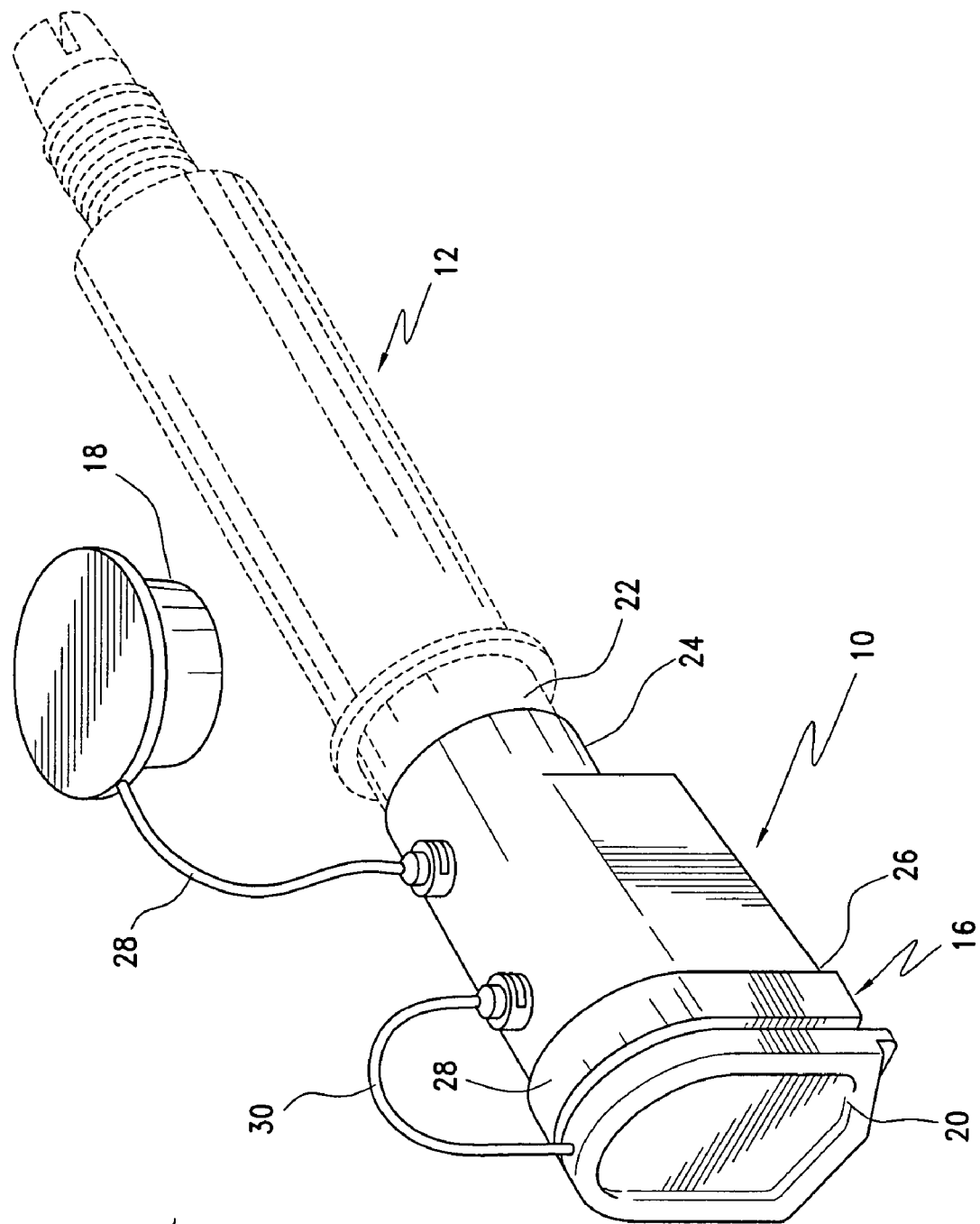
FIG. 1 is a side perspective view of the filter assembly, shown attached to a fuel checker, with the end cap attached to the filter housing.
Figure 2:
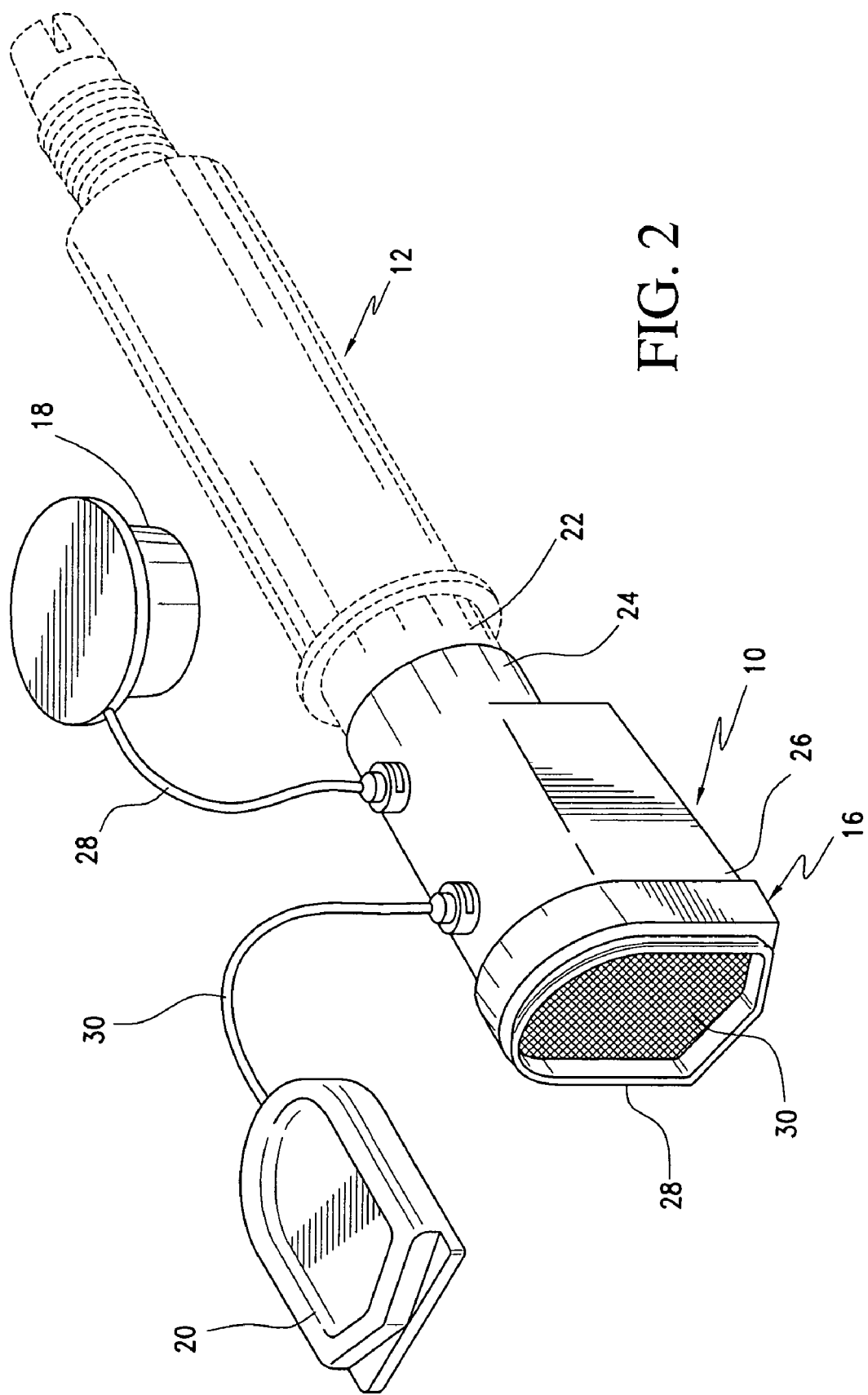
FIG. 2 is a side perspective view of the filter assembly showing the release of the end cap.
Figure 3:
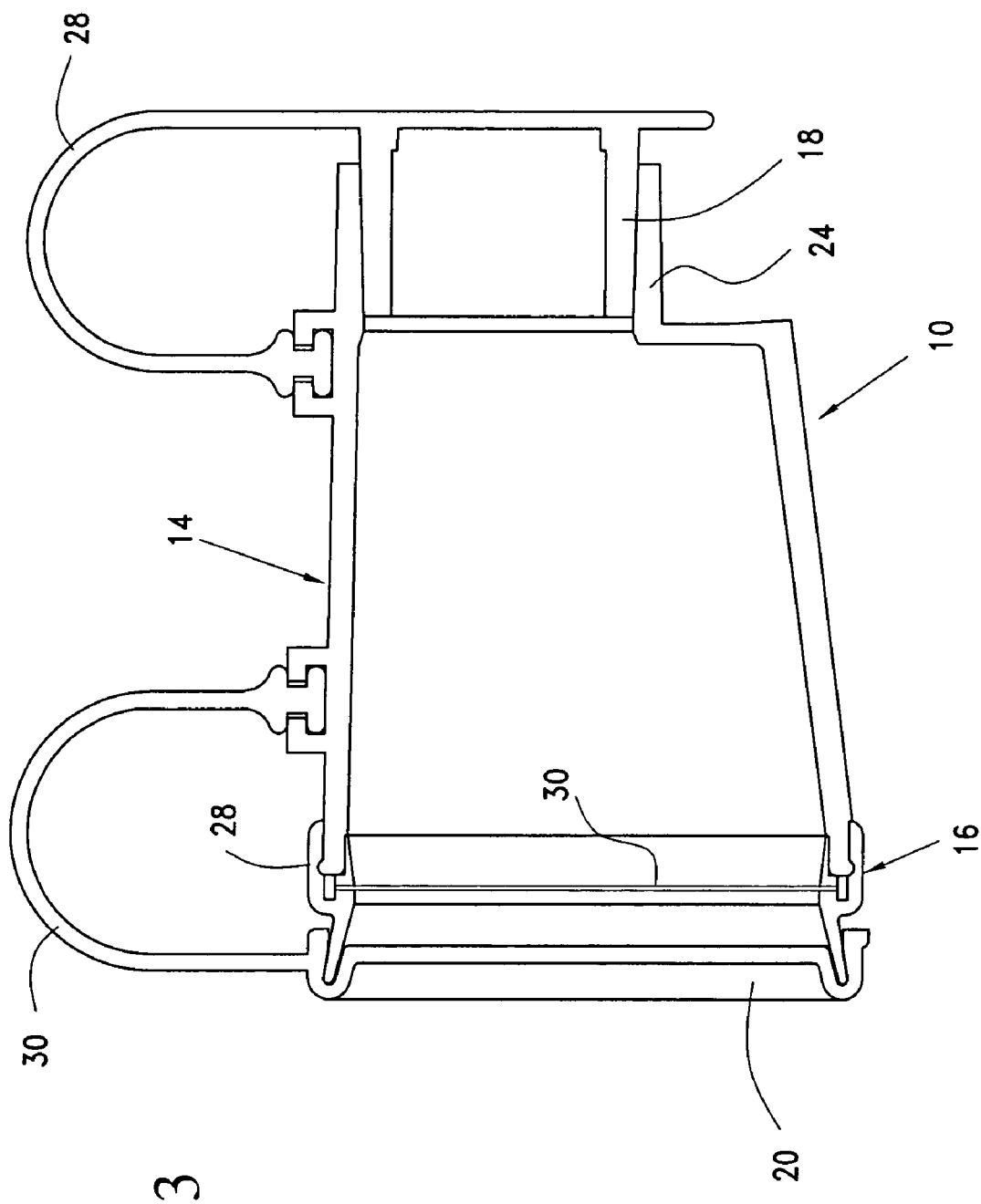
FIG. 3 is a side cross-sectional view of the filter assembly.

Referring now to the drawings and the characters of reference marked thereon, FIGS. 1–3 illustrate a preferred embodiment of the filter assembly of the present invention, designated generally as 10 shown attached to a fuel checker 12. The filter assembly 10 includes a filter housing, designated generally as 14, a removable screen assembly 16, a first protective cap 18, and a second protective cap 20.

The present invention is particularly adapted for use with present applicant's fuel checker described in U.S. Pat. No. 5,359,905, entitled Fuel Checker For Use With Pet Cock or Ball and Spring Drain Valves, incorporated by reference herein, in its entirety. The '905 fuel checker 12 is illustrated in phantom lines. It is formed of transparent molded plastic material. It has a slightly recessed outer surface 22 on an upper end portion thereof. The recessed outer surface 22 has a substantially circular cross-section.

The filter housing 14 includes a fuel receiving end portion 24 that has a substantially circular cross-section. It includes an annular interior surface 26 having a substantially circular cross-section thereon for cooperating with the recessed outer surface of the fuel checker 12 and providing a friction fit therewith. This allows the fuel receiving end portion 24 to be slidably mounted on the upper end portion of the fuel checker 12.

A fuel exiting end portion 26 is tapered to have an increasing cross-sectional area toward a distal end thereof. The filter housing 14 is preferably fabricated of transparent, molded plastic material such as cellulose acetate butyrate. The fuel receiving end portion has an outside diameter of about 1.2 inches. The height of the fuel exiting end portion is about 2 inches. It has a width of about 1.3 inches.

The removable screen assembly 16 is securely attachable to the fuel exiting end portion 26. As can best be seen in FIG. 3, the removable screen assembly 16 includes a flexible screen housing 28 that is pressed into position at the end of the fuel exiting end portion 26. The screen housing 28 is preferably formed of a plastic such as polypropylene. Although the screen assembly 16 is removable it is generally not removed unless its replacement is needed due to damage or contamination.

A filter screen 30 is supported by the flexible screen housing 28. The filter screen 30 provides separation of water and other contaminants. In a preferred implementation the filter screen 30 is stainless steel bolting cloth, the mesh is 145 per lineal inch, with a wire diameter of 0.0022 inch, and a width opening of 0.0047 inch, making it very close to a 120 micron filter.

The first protective cap 18 fits over the fuel receiving end portion for containing evaporative fumes while the filter assembly 10 is not being used. A flexible connecting member 28 is preferably utilized to attach the protective cap 18 to said filter housing 14. As shown in the figures, the connecting member 28 is preferably integral with the cap 18.

The second protective cap, i.e. end cap 20, fits over the screen assembly for containing evaporative fumes. As was the case with the other cap 18, a flexible connecting member 30 is utilized to attach the protective cap 20 to the filter housing 14.

In use, after a fuel sample is checked with the fuel checker 12, if a splashguard is used with the fuel checker 12, that splashguard is removed. Both caps 18, 20 are open when the filter assembly 10 is connected to the fuel checker 12. The contents are then poured back into the gas tank. If another sample is desired to be taken the filter assembly 10 is removed and then affixed again after the sample is taken.

The filter assembly 10 can be easily stored by connecting the caps 18, 20. Thus, fumes and residual fuel cannot leak. Since the fuel filter is relatively narrow it can be conveniently stowed in a seat pocket or side pocket of an airplane.

Figure 4:
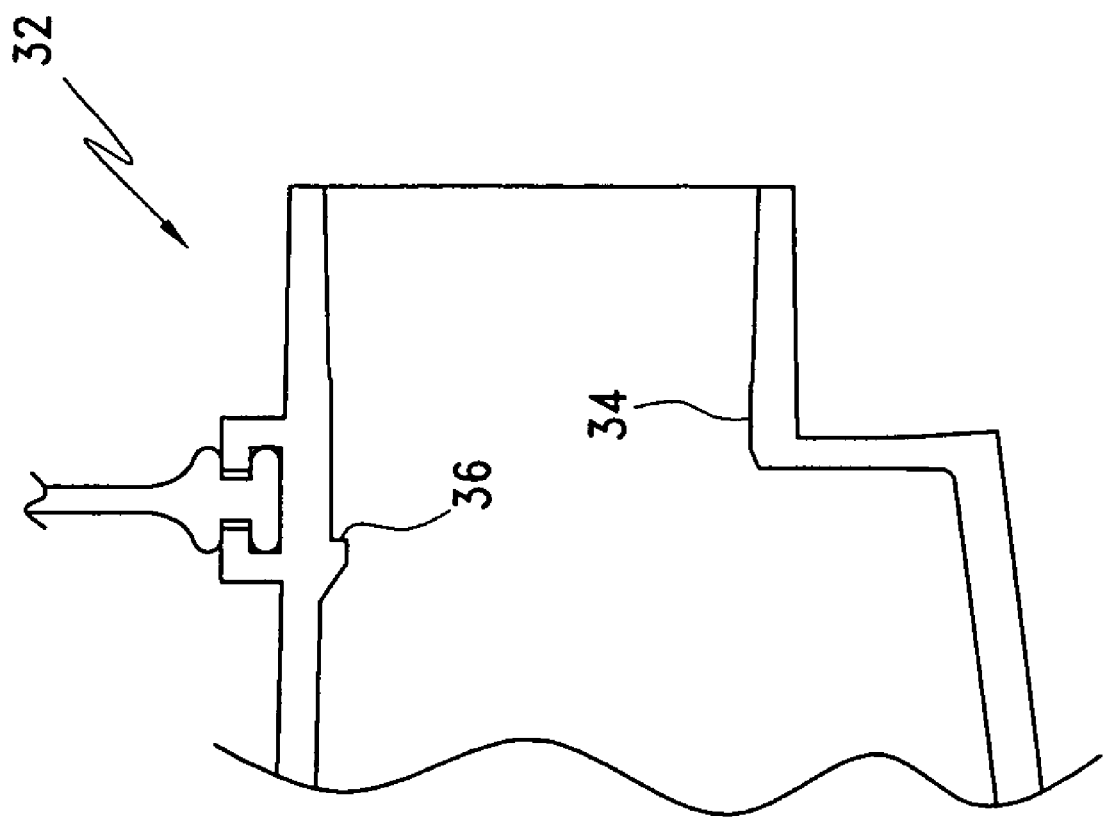
FIG. 4 is a side cross-sectional view of an alternate filter assembly with a step and stop for use with an ASA fuel checker.

Referring now to FIG. 4, an alternative filter assembly is illustrated, designated generally as 32. Filter assembly 32 has an annular interior surface with a step 34 and angle to accommodate the aircraft fuel tester known as ASA-AFT-1. A stop 36 cooperates with an end of the fuel checker to prevent longitudinal movement thereof.

Other embodiments and configurations may be devised without departing from the spirit of the invention and the scope of the appended claims.

What is claimed is:

1. A filter assembly for a fuel checker, said filter assembly, comprising:
   a) a filter housing, including a fuel receiving end portion and a fuel exiting end portion, said fuel receiving end portion being shaped to securely attach to a fuel checker, said filter housing defining a volume for containing checked fuel;
   b) a screen assembly securely attachable to said fuel exiting end portion, said removable screen assembly, comprising:
      i. a flexible screen housing; and,
      ii. a filter screen supported by said flexible screen housing, said filter screen being a barrier to water and desired particulate debris;
   c) a first protective cap for fitting over said fuel receiving end portion for containing evaporative fumes while the filter assembly is being stored; and,
   d) a second protective cap for fitting over said removable screen assembly and protecting said screen when the filter assembly is being stored.

2. The filter assembly of claim 1 wherein said fuel checker is of a type that includes a slightly recessed outer surface on an upper end portion thereof,
   said fuel receiving end portion including an annular interior surface thereon for cooperating with said recessed outer surface of said fuel checker and providing a friction fit therewith to allow said fuel receiving end portion to be slidably mounted on said upper end portion of said fuel checker.

3. The filter assembly of claim 1 wherein said fuel checker is of a type that includes a slightly recessed outer surface on an upper end portion thereof, the recessed outer surface being of substantially circular cross-section,
   said fuel receiving end portion having a substantially circular cross-section and including an annular interior surface with a substantially circular cross-section thereon for cooperating with said recessed outer surface of said fuel checker and providing a friction fit therewith to allow said fuel receiving end portion to be slidably mounted on said upper end portion of said fuel checker.

4. The filter assembly of claim 1 wherein said fuel checker is of a type that includes a slightly recessed outer surface on an upper end portion thereof of substantially circular cross-section,
   a) said fuel receiving end portion having a substantially circular cross-section and including an annular interior surface thereon for cooperating with said recessed outer surface of said fuel checker and providing a friction fit therewith to allow said fuel receiving end portion to be slidably mounted on said upper end portion of said fuel checker, and b) said fuel exiting end portion having a cross-sectional area larger than said fuel receiving end portion.

5. The filter assembly of claim 1, further comprising a first protective cap connecting member for attaching said first protective cap to said filter housing.

6. The filter assembly of claim 1, further comprising a second protective cap connecting member for attaching said second protective cap to said removable screen assembly.

7. The filter assembly of claim 1 wherein said fuel receiving end portion is substantially narrower than said fuel exiting end portion to maximize the cross-sectional area of said filter screen.

8. The filter assembly of claim 1 wherein said fuel exiting end portion is tapered to have an increasing cross-sectional area toward a distal end thereof to maximize the cross-sectional area of said filter screen.

9. The filter assembly of claim 1, wherein said filter screen comprises stainless steel material.

10. The filter assembly of claim 1, wherein said filter screen provides particulate debris filtration to approximately 120 microns.

11. The filter assembly of claim 1, wherein said filter housing is fabricated of transparent molded material.

12. The filter assembly of claim 1 wherein said fuel checker is of a type that includes a slightly recessed outer surface on an upper end portion thereof, said fuel receiving end portion including an annular interior surface thereon including a step for cooperating with said recessed outer surface of said fuel checker and providing a friction fit therewith to allow said fuel receiving end portion to be slidably mounted on said upper end portion of said fuel checker.

13. The filter assembly of claim 1 wherein said fuel checker is of a type that includes a slightly recessed outer surface on an upper end portion thereof, said fuel receiving end portion including an annular interior surface thereon including a step for cooperating with said recessed outer surface of said fuel checker and providing a friction fit therewith to allow said fuel receiving end portion to be slidably mounted on said upper end portion of said fuel checker, said annular interior surface further including a stop for cooperating with an end of said fuel checker to prevent longitudinal movement thereof.

14. The filter assembly of claim 1, wherein said screen assembly is removable.

* * * * *